United States Patent [19]
Moretz et al.

[11] Patent Number: 5,269,720
[45] Date of Patent: Dec. 14, 1993

[54] MOISTURE MANAGING BRASSIERE

[76] Inventors: Herbert L. Moretz, 20205 Lola Cir., Davidson, N.C. 28036; Daniel L. Brier, 33 Angelfish Cay Dr., Key Largo, Fla. 33037

[21] Appl. No.: 3,263

[22] Filed: Jan. 12, 1993

Related U.S. Application Data

[63] Continuation-in-part of Ser. No. 991,761, Dec. 17, 1992, which is a continuation-in-part of Ser. No. 945,677, Sep. 16, 1992, which is a continuation-in-part of Ser. No. 842,224, Feb. 26, 1992, which is a continuation-in-part of Ser. No. 791,066, Nov. 12, 1991, Pat. No. 5,217,782.

[51] Int. Cl.$^5$ ............................................. A41C 3/00
[52] U.S. Cl. ........................................ 450/37; 450/34; 450/36; 450/74; 450/76; 450/32; 2/73; 2/267; 604/358
[58] Field of Search ............... 450/30, 31, 32, 36, 450/38, 34, 53-57, 65, 67, 74, 76; 2/73, 267; 604/358

[56] References Cited

U.S. PATENT DOCUMENTS

| | | | |
|---|---|---|---|
| 3,203,424 | 8/1965 | Garutso | 450/36 |
| 4,390,024 | 6/1983 | Williams | 450/36 |
| 4,640,287 | 2/1987 | Anderson et al. | 450/36 |
| 5,149,336 | 9/1992 | Clarke et al. | 604/358 |

*Primary Examiner*—Clifford D. Crowder
*Assistant Examiner*—Gloria Hale
*Attorney, Agent, or Firm*—W. Thad Adams, III

[57] ABSTRACT

A moisture management brassiere which includes a brassiere body, including a body and back strap. The body and back strap are formed of a stretch fabric having a moisture transport fabric layer constructed of hydrophobic yarns which define a first fabric face for residing in skin contact and for wicking moisture away from the skin. A moisture dispersal fabric layer is provided, and is constructed of hydrophilic yarns and defines a second fabric face for residing in spaced-apart relation from the skin during garment wear. The moisture dispersal fabric layer receives moisture from the hydrophobic moisture transport layer. Stretch yarns provide stretch to the back strap. A pair of breast enclosing and supporting cups are attached to the back strap of the brassiere. Each of the cups is constructed of a moisture transport fabric layer constructed of hydrophobic yarns which define a first fabric face for residing in skin contact during garment wear and for wicking moisture away from the skin. A moisture dispersal fabric layer constructed of hydrophilic yarns and defining a second fabric face is provided for residing in spaced-apart relation from the skin during garment wear and for receiving moisture from the hydrophobic moisture transport layer. A liquid impermeable, vapor permeable fabric defining the outermost fabric face resides adjacent to the second hydrophilic moisture dispersal fabric layer.

9 Claims, 2 Drawing Sheets

MOISTURE MANAGING BRASSIERE

This application is a continuation-in-part of application Ser. No. 991,761, filed on Dec. 17, 1992, which is a continuation-in-part of Ser. No. 945,677, filed on Sep. 16, 1992, which is a continuation-in-part of Ser. No. 842,224, filed on Feb. 26, 1992, which is a continuation-in-part of application Ser. No. 791,066, filed on Nov. 12, 1991, now U.S. Pat. No. 5,217,782.

TECHNICAL FIELD and BACKGROUND of the INVENTION

This invention relates to moisture managing undergarments for women, specifically to brassieres worn by women during the late stages of pregnancy, immediately following delivery and especially during the lactation period when an infant child is being breast-fed by the lactating mother.

The female mammary gland is a somewhat conical mass of glandular tissue traversed and supported by strands of fibrous tissue and covered by a thick layer of fat. Each gland is situated in the superficial fascia covering the anterior aspect of the thorax and usually extends from the level of the second or third rib to that of the sixth rib. The hemispherical projection formed by the gland lies upon the superficial aspect of the pectoralis major and to a lesser extent upon the serratus anterior muscle. Near the summit of each mammary gland and usually at the level of the fourth or fifth rib is a papilla mammae, or nipple from which the mother's milk flows.

Breast feeding has enjoyed a recent recurrence of popularity. It is now recognized that breast feeding has a number of significant advantages over bottle feeding. Mother's milk is always the right temperature, and contains the proper proportions of carbohydrate, protein and fat. Mother's milk is free from bacterial contamination and contains natural antibodies to numerous infant diseases.

This recurrence of popularity has, however, run squarely into the ever-increasing tendency for women to combine careers with child-rearing. This presents problems relating to proper garment selection and wear, and embarrassment which may result from leakage from the breasts through to outer garments.

During pregnancy, particularly in the latter stages, the breast enlarges under the influence of hormonal changes incident to pregnancy, and in preparation for lactation. Upon delivery of the child, the breast is prepared to dispense milk from tiny openings in the nipple, unless suppressed.

During these stages of pregnancy and motherhood, it is not uncommon for women to experience leakage from the nipple. This invention addresses problems associated with both the increased size and weight of the breast during and after pregnancy, and also with the leakage that often occurs at times, during the work day, for example, when a child cannot be fed or the clothing changed. This often results in embarrassing wet spots on clothing and unwanted wetness next to the skin. This condition can cause odor, chafing, irritation and an environment conducive to the growth of bacteria and fungus.

The fabrics from which this moisture managing brassiere is constructed are intended to quickly move moisture away from the skin of the wearer and slow the outward movement of the moisture while at the same time enhancing the dispersion of the moisture to those fibers of the fabric that do not touch the skin. The fabric also permits moisture in the form of vapor to migrate to the outer surface of the fabric where evaporation will occur.

The result of these functions is to keep the skin as dry as possible while preventing outer clothing from becoming wet from milk or perspiration leaking through the brassiere from inside to outside.

SUMMARY OF THE INVENTION

Therefore, it is an object of the invention to provide a moisture-management brassiere.

It is another object of the invention to provide a brassiere which disperses leakage of milk and perspiration throughout a sufficiently wide area so as to retard leak-through to outer garments.

It is another object of the invention to provide a brassiere which wicks milk and perspiration away from the skin, in order to increase comfort for the wearer.

It is another object of the invention to provide a brassiere which has cups for enclosing and supporting the breasts which are attached to the body components of the garment by means of a moisture management stretch fabric.

It is another object of the invention to provide a brassiere which has cups which stretch to accommodate the breast when enlarged, and which then relax to provide continuous support as the breast is emptied of milk and thus reduced in size.

These and other objects of the present invention are achieved in the preferred embodiments disclosed below by providing a moisture management brassiere which includes a brassiere body, including a thorax-encircling back strap for holding the brassiere in position on the wearer. The back strap is formed of a stretch fabric having a moisture transport fabric layer constructed of hydrophobic yarns which define a first fabric face for residing in skin contact during garment wear and for wicking moisture away from the skin. A moisture dispersal fabric layer is provided, and is constructed of hydrophilic yarns and defines a second fabric face for residing in spaced-apart relation from the skin during garment wear. The moisture dispersal fabric layer receives moisture from the hydrophobic moisture transport layer. Stretch yarns provide stretch to the back strap.

The brassiere also includes a pair of breast enclosing and supporting cups attached to the back strap of the brassiere. Each of the cups is constructed of a moisture transport fabric layer constructed of hydrophobic yarns which define a first fabric face for residing in skin contact during garment wear and for wicking moisture away from the skin. A moisture dispersal fabric layer constructed of hydrophilic yarns and defining a second fabric face is provided for residing in spaced-apart relation from the skin during garment wear and for receiving moisture from the hydrophobic moisture transport layer. A liquid impermeable, vapor permeable fabric defining the outermost fabric face resides adjacent to the second hydrophilic moisture dispersal fabric layer.

A pair of shoulder straps is attached by one end to respective cups and by respective opposite ends to the back-strap to provide further support to the breasts.

According to one preferred embodiment of the invention, the hydrophobic yarn of the moisture transport layer of the back strap and the cups is chosen from the fiber group consisting of polyester and polypropylene.

According to another preferred embodiment of the invention, the hydrophilic yarn of the moisture dispersal fabric layer is chosen from the fiber group consisting of hydrophilic nylon, cotton, rayon and blends of hydrophilic nylon and regular nylon.

According to yet another preferred embodiment of the invention, the yarn of the liquid impermeable, vapor permeable fabric layer is chosen from the fiber group consisting of polyester and nylon microfiber.

According to yet another preferred embodiment of the invention, the yarn of the moisture management stretch fabric of the body of the brassiere connecting the cups to the back strap of the brassiere is chosen from the group consisting of blends of nylon/spandex, polyester/spandex and cotton/spandex.

According to yet another preferred embodiment of the invention, the moisture transport fabric layer of the brassiere cups is constructed of hydrophobic polyester yarns formed of fibers having a high surface area in relation to volume.

According to yet another preferred embodiment of the invention, the moisture transport fabric layer of the brassiere cups is constructed of a "push-pull" integrated knit fabric having hydrophobic polyester fibers on the inner fabric face next to the skin of the wearer and hydrophilic nylon on the obverse fabric face.

According to yet another preferred embodiment of the invention, the brassiere includes means for detaching a part of the cup from the body of the brassiere for exposing a breast for nursing.

According to one preferred embodiment of the invention, a moisture management brassiere is provided, which includes a brassiere body, including a thorax-encircling back strap for holding the brassiere in position on the wearer. The back strap is constructed of a stretch fabric having a moisture transport fabric layer constructed of hydrophobic yarns which define a first fabric face for residing in skin contact during garment wear and for wicking moisture away from the skin, wherein the hydrophobic yarn of the moisture transport layer is chosen from the fiber group consisting of polyester and polypropylene.

The back strap fabric also has a moisture dispersal fabric layer constructed of hydrophilic yarns and defining a second fabric face for residing in spaced-apart relation from the skin during garment wear and for receiving moisture from the hydrophobic moisture transport layer, wherein the hydrophilic yarn of the moisture dispersal fabric layer is chosen from the fiber group consisting of hydrophilic nylon, cotton, rayon and blends of hydrophilic nylon and regular nylon. Stretch yarns are incorporated into the fabric for providing stretch to the back strap.

A pair of breast enclosing and supporting cups are attached to the back strap of the brassiere and are constructed of a moisture transport fabric layer constructed of hydrophobic yarns which define a first fabric face for residing in skin contact during garment wear and for wicking moisture away from the skin. The hydrophobic yarn of the moisture transport layer is chosen from the fiber group consisting of polyester and polypropylene. A moisture dispersal fabric layer is provided, and is constructed of hydrophilic yarns defining a second fabric face for residing in spaced-apart relation from the skin during garment wear and for receiving moisture from the hydrophobic moisture transport layer. The hydrophilic yarn of the moisture dispersal fabric layer is chosen from the fiber group consisting of hydrophilic nylon, cotton, rayon and blends of hydrophilic nylon and regular nylon.

A liquid impermeable, vapor permeable fabric outermost fabric face resides adjacent to the second hydrophilic moisture dispersal fabric layer of the cups.

A pair of shoulder straps are attached by one end to respective cups and by respective opposite ends to the back-strap to provide further support to the breasts. The shoulder straps are constructed of a stretch fabric.

BRIEF DESCRIPTION OF THE DRAWINGS

Some of the objects of the invention have been set forth above. Other objects and advantages of the invention will appear as the invention proceeds when taken in conjunction with the following drawings, in which.

DESCRIPTION OF THE PREFERRED EMBODIMENT AND BEST MODE

Figure 1:
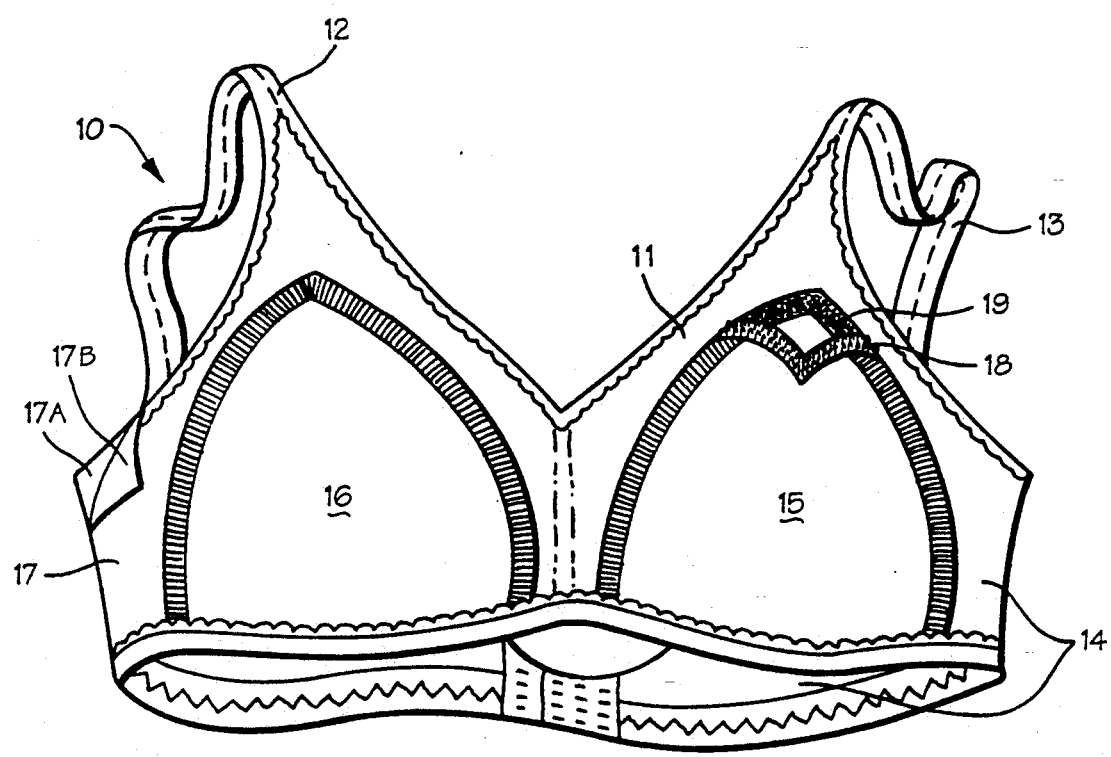
FIG. 1 is a moisture managing brassiere according to an embodiment of the present invention.

Referring now specifically to the drawings, a moisture managing brassiere according to a preferred embodiment of the invention is shown in FIG. 1, and broadly indicated at reference numeral 10.

The brassiere 10 is intended for use by women in the late stages of pregnancy and during the period of lactation following delivery. Brassiere 10 is constructed of a body portion 11 which includes a pair of shoulder straps 12 and 13, a back strap 14 and a pair of cups 15 and 16. The cups 15 and 16 may be designed so that they can be partially detached to permit access to the breast for nursing. By way of example, complementary hook and loop fastening elements 18 and 19 are provided on the upper perimeter of the cups 15 and 16. Thus, the top of the cups 15 and 16 can be folded down towards the bodice of the brassiere 10 and out of the way so that the infant can nurse. When nursing is complete, the cup 15 or 16 is folded back into position and secured in place by pressing the hook elements 18 into the loop elements 19. Of course, other fastening elements, such as snaps, may also be used.

The shoulder straps 12 and 13 are constructed of a stretch fabric, such as a warp knitted elastic fabric disclosed in applicant's prior application Ser. No. 07/991,761, filed on Dec. 17, 1992.

The body 11 and back strap 14 are formed of a stretch fabric 17 having a moisture transport fabric layer 17A constructed of hydrophobic yarns which define a first fabric face residing in skin contact during garment wear. This fabric layer 17A is intended to wick moisture away from the skin. The fabric layer 17A may be polyester or polypropylene.

A moisture dispersal fabric layer 17B is constructed of hydrophilic yarns and defines a second fabric face for residing in spaced-apart relation from the skin during garment wear. Layer 17B receives moisture from the hydrophobic moisture transport layer 17A. The hydrophilic yarn of the moisture dispersal fabric layer 17B may be nylon, cotton, rayon and blends of hydrophilic nylon and conventional nylon; Stretch yarns are incorporated into the fabric 17 for providing stretch to the body 11 and back strap 14.

The body 11 and back strap 14 are preferably constructed of moisture management stretch fabric which includes approximately 85% polyester fibers and 15% spandex fibers. The polyester fibers are designed for relatively great surface area in relation to volume, such as Coolmax (R) fibers produced by the DuPont Corporation, with channels running longitudinally along the shaft of the fiber to enhance the wicking or transport of moisture.

Figure 2:
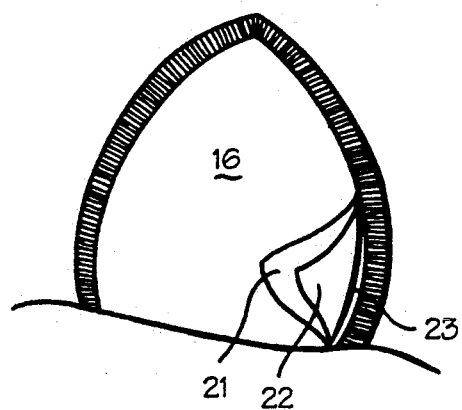
FIG. 2 is a view of the inside of the cup of the brassiere in FIG. 1 which would hold the wearer's left breast.

The brassiere cups 15 and 16 are constructed of a multi-layer fabric system described in detail in FIG. 2.

In addition to supporting the breast, the brassiere cup 16 shown in FIG. 2 includes a hydrophobic fabric layer 21 to reside next to the skin to quickly transport moisture away from the skin. Fabric layer 21 is comprised of polyester wicking fibers such as Coolmax (R) that are designed specifically to transport moisture. An intermediate fabric layer 22 is placed adjacent to the outer fabric face of fabric layer 21, and is formed of a hydrophilic dispersal fabric layer that works to keep the moisture away from the skin by providing hydrophilic fibers to receive moisture transported to its surface by hydrophobic fabric layer 21. Thus fabric layer 22 spreads moisture along its fibers and thereby enhances evaporation and reduces the likelihood of liquid moisture penetrating to stain outer clothing.

The brassiere cup 16 also includes a third outermost fabric layer 23 that is liquid impermeable but vapor permeable. This polyester microfiber fabric layer blocks the outward flow of liquid, yet allows the moisture that has been temporarily dispersed throughout the dispersal fabric layer 22 to pass through in vapor form (evaporate). Fabric layer 23 forms the outer surface or shell of the brassiere cup 16.

Figure 3:
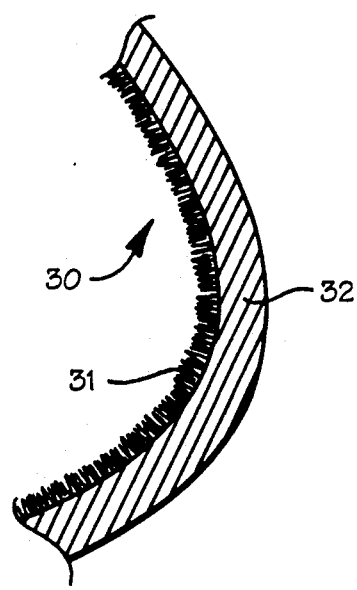
FIG. 3 is a cross-sectional view of a "push-pull" knit fabric that integrates hydrophobic fibers and hydrophilic fibers according to an embodiment of the invention.

FIG. 3 shows a cross-sectional view of a fabric of a brassiere cup 30 of a different embodiment of the invention than that shown in FIG. 2. Brassiere cup 30 is constructed of a "push-pull" bi-component warp knit fabric formed of hydrophobic polyester wicking fibers which form the innermost fabric layer 31 for residing next to the skin of the wearer, and an integrally knit outer fabric layer 32 formed of hydrophilic fibers such as Hydrofil (R) produced by Allied Fibers. Fabric 30 combines in one integrally knit fabric the same fibers and functions of fabric layers 21 and 22 of cup 16 illustrated in FIG. 2.

Cup 30 may be used instead of cup 16, while retaining the hydrophilic fabric layer 22 in the moisture managing fabric system used in the brassiere cup 16.

Figure 4:
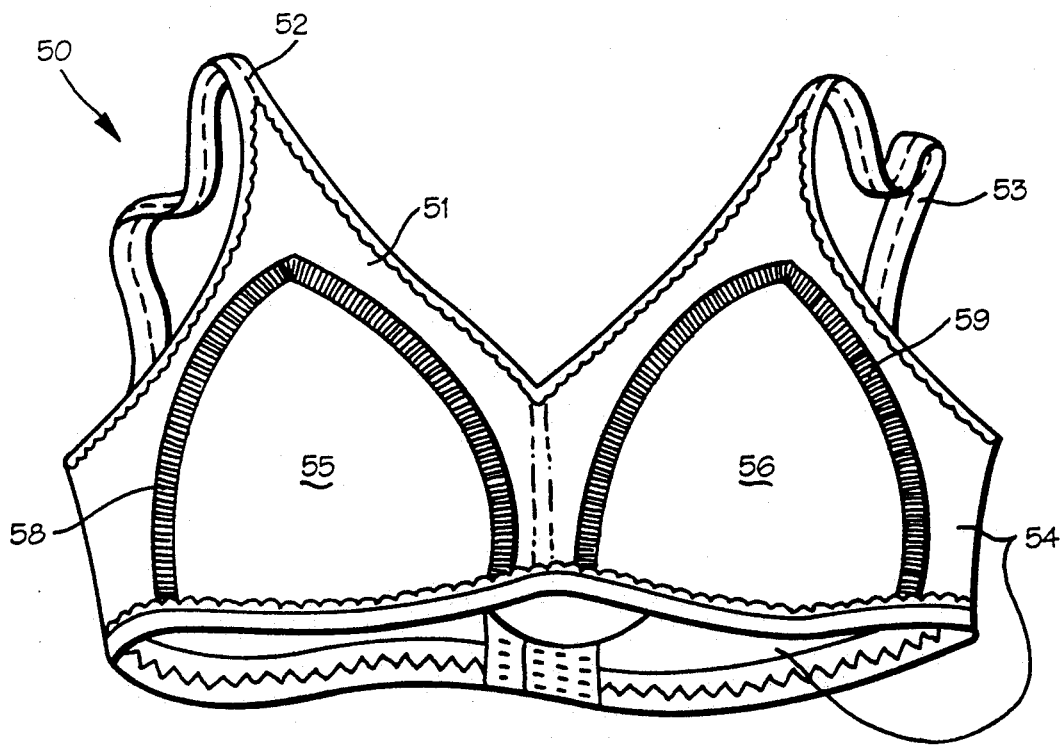
FIG. 4 is a moisture managing brassiere according to another embodiment of the present invention.

In accordance with another embodiment as shown in FIG. 4, brassiere 50 is constructed of a body portion 51 which includes a pair of shoulder straps 52 and 53, a back strap 54 which is attached by hooks in the back, and a pair of cups 55 and 56. Cups 55 and 56 are set into the body 51 with respective elastic gores 58 and 59. Gores 58 and 59 are constructed of a moisture management fabric comprised of approximately 75% Coolmax (R) polyester and 25% spandex fibers. This is a smooth fabric with the capacity to stretch approximately 75% in any direction, such as that manufactured by Charbert, Inc. or by Lida, Inc. This fabric provides support for the breast yet allows the cups 55 and 56 to expand as the breasts are enlarged with fluid and to contract while maintaining support as the breast contracts as a result of the removal of fluid. Brassiere 50 has sufficient stretch so that it can simply be pulled off of one shoulder to a degree necessary to expose the breast, with the weight of the breast bearing on the top of the cup 55 or 56 to keep it from interfering with nursing. When nursing is complete, the breast is merely placed back in the cup 55 or 56 by pulling the cup upwardly over the breast.

The body 11 and back straps 14 are constructed as described above with reference to FIG. 1. The brassiere cups 55 and 56 are constructed of a multi-layer fabric system as described above with reference to FIG. 2.

A moisture management brassiere is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

We claim:

1. A moisture management reusable and launderable brassiere, comprising:
   (a) a brassiere body, including a thorax-encircling back strap for holding the brassiere in position on the wearer, comprising:
      (1) a stretch fabric having a moisture transport fabric layer constructed of hydrophobic yarns which define a first fabric face for residing in skin contact during garment wear and for wicking moisture away from the skin;
      (2) a moisture dispersal fabric layer constructed of hydrophilic yarns and defining a second fabric face for residing in spaced-apart relation from the skin during garment wear and for receiving moisture from the hydrophobic moisture transport layer; and
      (3) stretch yarns in the back strap for providing stretch to the back strap;
   (b) a pair of breast enclosing and supporting cups attached to the back strap of the brassiere and comprising:
      (1) a moisture transport fabric layer constructed of hydrophobic yarns which define a first fabric face for residing in skin contact during garment wear and for wicking moisture away from the skin;
      (2) a moisture dispersal fabric layer constructed of hydrophilic yarns and defining a second fabric face for residing in spaced-apart relation from the skin during garment wear and for receiving moisture from the hydrophilic moisture transport layer; and
      (3) a liquid impermeable, vapor permeable fabric outermost fabric face residing adjacent to the second hydrophilic moisture dispersal fabric layer;
   (c) a pair of shoulder straps attached by one end to respective cups and by respective opposite ends to the back-strap to provide further support to the breasts.

2. A brassiere according to claim 1, wherein the hydrophobic yarn of the moisture transport layer of the back strap and the cups is chosen from the fiber group consisting of polyester and polypropylene.

3. A brassiere according to claim 1, wherein the hydrophilic yarn of the moisture dispersal fabric layer is chosen from the fiber group consisting of hydrophilic nylon, cotton, rayon and blends of hydrophilic nylon and conventional nylon.

4. A brassiere according to claim 3, wherein the yarn of the liquid impermeable, vapor permeable fabric layer is chosen from the fiber group consisting of polyester and nylon microfiber.

5. A brassiere according to claim 4, wherein the yarn of the moisture management stretch fabric of the body of the brassiere connecting the cups to the back strap of the brassiere is chosen from the group consisting of blends of nylon/spandex, polyester/spandex and cotton/spandex.

6. A brassiere according to claim 1, the moisture transport fabric layer of the brassiere cups is constructed of hydrophobic polyester yarns formed of fibers having a high surface area in relation to volume.

7. A brassiere according to claim 1, wherein the moisture transport fabric layer of the brassiere cups is constructed of an integrated knit fabric having hydrophobic polyester fibers on the first fabric face next to the skin of the wearer and hydrophilic nylon on the second, obverse fabric face.

8. A brassiere according to claim 1, 2, 3, 4, 5, 6, or 7, and including means for detaching a part of the cup from the body of the brassiere for exposing a breast for nursing.

9. A moisture management reusable and launderable brassiere, comprising:
   (a) a brassiere body, including a thorax-encircling back strap for holding the brassiere in position on the wearer, comprising:
      (1) a stretch fabric having a moisture transport fabric layer constructed of hydrophobic yarns which define a first fabric face for residing in skin contact during garment wear and for wicking moisture away from the skin, wherein the hydrophobic yarn of the moisture transport layer is chosen from the fiber group consisting of polyester and polypropylene;
      (2) a moisture dispersal fabric layer constructed of hydrophilic yarns and defining a second fabric face for residing in spaced-apart relation from the skin during garment wear and for receiving moisture from the hydrophobic moisture transport layer, wherein the hydrophilic yarn of the moisture dispersal fabric layer is chosen from the fiber group consisting of hydrophilic nylon, cotton, rayon and blends of hydrophilic nylon and conventional nylon; and
      (3) stretch yarns in the back strap for providing stretch to the back strap;
   (b) a pair of breast enclosing and supporting cups attached to the back strap of the brassiere and comprising:
      (1) a moisture transport fabric layer constructed of hydrophobic yarns which define a first fabric face for residing in skin contact during garment wear and for wicking moisture away from the skin, wherein the hydrophobic yarn of the moisture transport layer is chosen from the fiber group consisting of polyester and polypropylene;
      (2) a moisture dispersal fabric layer constructed of hydrophilic yarns and defining a second fabric face for residing in spaced-apart relation from the skin during garment wear and for receiving moisture from the hydrophobic moisture transport layer, wherein the hydrophilic yarn of the moisture dispersal fabric layer is chosen from the fiber group consisting of hydrophilic nylon, cotton, rayon and blends of hydrophilic nylon and conventional nylon; and
      (3) a liquid impermeable, vapor permeable fabric comprising an outermost fabric face residing adjacent to the second hydrophilic moisture dispersal fabric layer; and
   (c) a pair of shoulder straps attached by one end to respective cups and by respective opposite ends to the back-strap to provide further support to the breasts, said shoulder straps comprising a stretch fabric.

* * * * *